(12) United States Patent
Goto et al.

(10) Patent No.: US 7,157,599 B2
(45) Date of Patent: Jan. 2, 2007

(54) METHOD OF PRODUCING α,β-UNSATURATED CARBOXYLIC ACID COMPOUNDS

(75) Inventors: Fumisato Goto, Ibaraki (JP); Hirotada Kakiya, Ibaraki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 11/149,241

(22) Filed: Jun. 10, 2005

(65) Prior Publication Data

US 2005/0277786 A1   Dec. 15, 2005

(30) Foreign Application Priority Data

Jun. 14, 2004   (JP)   ............................. 2004-175350

(51) Int. Cl.
 *C07C 57/18* (2006.01)
 *C07C 35/00* (2006.01)
(52) U.S. Cl. ........................ 562/598; 562/599
(58) Field of Classification Search ................ 562/598, 562/599
 See application file for complete search history.

(56) References Cited

U.S. PATENT DOCUMENTS 4,677,225 A   6/1987   Niizuma et al.

FOREIGN PATENT DOCUMENTS

WO   WO 98/29379 A1   7/1998

*Primary Examiner*—Thurman K. Page
*Assistant Examiner*—Karl Puttlitz
(74) *Attorney, Agent, or Firm*—Sughrue Mion, PLLC

(57) ABSTRACT

There is disclosed a method of producing α,β-unsaturated carboxylic acid of formula (3)

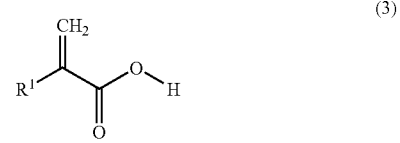

(3)

wherein $R^1$ denotes a hydrogen atom, an alkyl group, an aryl group, an aralkyl group, an alkenyl group or an alkynyl group,
which method comprises reacting a carboxylic acid of formula (1)

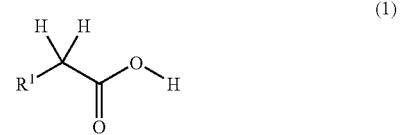

(1)

wherein $R^1$ denotes the same as the above, or carboxylic anhydride of formula (2)

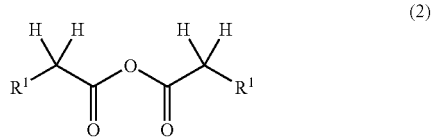

(2)

wherein $R^1$ denotes the same as the above, with a methylenating agent in a presence of a catalyst containing metal of Group 13 of the Periodic Table of Elements in the amount of not more than 5 weight %.

8 Claims, No Drawings

METHOD OF PRODUCING α,β-UNSATURATED CARBOXYLIC ACID COMPOUNDS

FIELD OF THE INVENTION

The present invention relates to method of producing α,β-unsaturated carboxylic acid compounds such as α,β-unsaturated carboxylic acid or α,β-unsaturated carboxylic ester, acrylic acid or methacrylic acid as well as methyl acrylate and methyl methacrylate, which are important compounds as raw materials for acrylate resin monomer.

BACKGROUND OF THE INVENTION

Among α,β-unsaturated carboxylic acid or α,β-unsaturated carboxylic ester, particularly important methacrylic acid and methyl methacrylic ester have conventionally been produced widely through a route via acetone cyanohydrin obtained by reacting acetone with hydrocyanic acid.

There was also disclosed a method of producing α,β-unsaturated carboxylic acid or ester by contacting a carboxylic acid, carboxylic ester or carboxylic anhydride with formaldehyde or formaldehyde source by using a catalyst containing niobium oxide (JP2001-507697W, which is an equivalent of WO98/29379). In this method, however, moisture sensitive and expensive niobium fluoride was required. A method of producing acrylic acid or methacrylic acid using a solid catalyst having an acid site having acid strength of $pKa \leq -3.0$ has been proposed (see JP-A-60-246342, which is equivalent of U.S. Pat. No. 4,677,225) and particularly disclosed therein is a method of using silica alumina containing $Al_2O_3$ in the amount of 13 to 28%, which showed insufficient selectivity.

DETAILED DESCRPTION OF THE INVENTION

According to the method of the present invention α,β-unsaturated carboxylic acid or α,β-unsaturated carboxylate is produced with good selectivity.

An aspect of the present invention relates to a method of producing α,β-unsaturated carboxylic acid of formula (3)

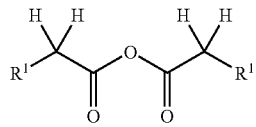

wherein $R^1$ denotes a hydrogen atom, an alkyl group, an aryl group, an aralkyl group, an alkenyl group or an alkynyl group, which method comprises reacting a carboxylic acid of formula (1)

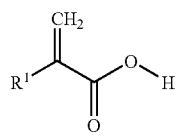

wherein $R^1$ denotes the same as the above, or a carboxylic anhydride of formula (2)

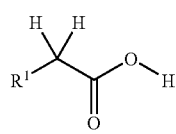

wherein $R^1$ denotes the same as the above, with a methylenating agent in the presence of a catalyst containing a metal of Group 13 of the Periodic Table of Elements in the amount of not more than 5 weight %; and another aspect of the invention relates to a method of producing α,β-unsaturated carboxylate of formula (5)

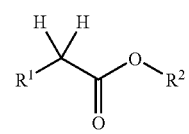

wherein $R^1$ denotes a hydrogen atom, an alkyl group, an aryl group, an aralkyl group, an alkenyl group or an alkynyl group, and $R^2$ denotes an alkyl group, an aryl group, an aralkyl group or an alkenyl group, which method comprises reacting a carboxylate of formula (4)

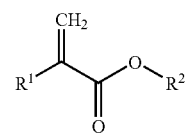

wherein $R^1$ and $R^2$ denote the same as the above, with a methylenating agent in the presence of a catalyst containing a metal of Group 13 of the Periodic Table of Elements in the amount of not more than 5 weight %.

DETAILED DESCRIPTION OF THE INVENTION

The present invention is hereinafter detailed.

A description will be made to $R^1$ and $R^2$ groups. The carboxylic acid of formula (1), the carboxylic anhydride of formula (2), the α,β-unsaturated carboxylic acid of formula (3), the carboxylate of formula (4), and α,β-unsaturated carboxylate of formula (5) are hereinafter referred to as carboxylic acid (1), carboxylic anhydride (2), α,β-unsaturated carboxylic acid (3), carboxylate (4), and α,β-unsaturated carboxylate (5) respectively.

Examples of the alkyl group represented by $R^1$ or $R^2$ include, for example, a C1–10 alkyl group, which may be linear, branched or cyclic, such as methyl, ethyl, propyl, butyl, cyclopentyl, cyclohexyl, pentyl, hexyl, heptyl, octyl nonyl or decyl.

Examples of the aryl group represented by $R^1$ or $R^2$ include, for example, a C6–10 aryl group such as phenyl, tolyl, or naphtyl.

Examples of the aralkyl group represented by $R^1$ include, for example, a C7–11 aralkyl group such as benzyl, phenylethyl, phenylpropyl, naphthylmethyl or the like.

Examples of the alkenyl group represented by $R^1$ or $R^2$ include, for example, a C2–10 alkenyl group, which may be linear, branched or cyclic, such as vinyl, propenyl, butenyl, pentenyl, hexenyl, cyclohexenyl, heptenyl, octenyl, nonenyl, or decenyl.

Examples of the alkynyl group represented by $R^1$ include, for example, a C2–10 alkynyl group, which may be linear, or branched, such as acetylenic, propynyl, butynyl, pentynyl, hexynyl, heptynyl, octynyl, nonynyl, or decynyl.

Preferably $R^1$ represents hydrogen and the C1–10 alkyl group, and more preferably hydrogen and the C1–3 alkyl group in carboxylic acid (1), carboxylic anhydride (2), α,β-unsaturated carboxylic acid (3), carboxylate (4), and α,β-unsaturated carboxylate (5).

Preferably $R^2$ represents the C1–10 alkyl group, and more preferably the C1–3 alkyl group in carboxylic acid (1), carboxylic anhydride (2), α,β-unsaturated carboxylic acid (3), carboxylate (4), and α,β-unsaturated carboxylate (5).

Specific examples of the carboxylic acid (1) wherein $R^1$ is hydrogen or alkyl include, for example, acetic acid, propionic acid, butyric acid, valeric acid, 3-methylbutanoic acid, caproic acid, heptanoic acid, caprylic acid, nonanoic acid, capric acid and undecanoic acid.

Examples of the carboxylic anhydride (2) wherein $R^1$ is hydrogen or alkyl include, for example, acetic anhydride, propionic anhydride, butyric anhydride, valeric anhydride, 3-methylbutanoic anhydride, caproic anhydride, heptanoic anhydride, caprylic anhydride, nonanoic anhydride, capric anhydride and undecanoic anhydride.

Examples of the carboxylic acid (1) wherein $R^1$ is aryl include, for example, phenylacetic acid, para-tolylacetic acid and naphthylacetic acid.

Examples of the carboxylic anhydride (2) wherein $R^1$ is aryl include, for example, phenylacetic anhydride, para-toluylacetic anhydride and naphthylacetic anhydride.

Examples of carboxylic acid (1) wherein $R^1$ is aralkyl include, for example, 3-phenylpropionic acid.

Examples of carboxylic anhydride (2) wherein $R^1$ is aralkyl include, for example, 3-phenylpropionic anhydride.

Examples of the carboxylic acid (1) wherein $R^1$ is alkenyl include, for example, vinylacetic acid, 4-pentenoic acid and 10-undecenoic acid.

Examples of the carboxylic anhydride (2) wherein $R^1$ is alkenyl include, for example, vinylacetic anhydride, 4-pentenoic anhydride and 10-undecenoic anhydride.

Examples of carboxylic acid (1) wherein $R^1$ is alkynyl include, for example, 3-butynoic acid, 3-pentynoic acid and 3-hexynoic acid.

Examples of the carboxylic anhydride (2) wherein $R^1$ is alkynyl include, for example, 3-butynoic anhydride, 3-pentynoic anhydride and 3-hexynoic anhydride.

Preferred carboxylic acid (1) are acetic acid and propionic acid, more preferred is propionic acid.

Preferred carboxylic anhydride (2) are acetic anhydride and propionic anhydride, more preferred is propionic anhydride.

Examples of the carboxylate (4) include, for example, methyl acetate, ethyl acetate, propyl acetate, butyl acetate, pentyl acetate, hexyl acetate, cyclohexyl acetate, heptyl acetate, octyl acetate, nonyl acetate, decyl acetate, phenyl acetate, naphthyl acetate, tolyl acetate, benzyl acetate, phenylethyl acetate, vinyl acetate, allyl acetate, methyl propionate, ethyl propionate, propyl propionate, butyl propionate, pentyl propionate, hexyl propionate, cyclohexyl propionate, heptyl propionate, octyl propionate, nonyl propionate, decyl propionate, phenyl propionate, naphthyl propionate, tolyl propionate, benzyl propionate, phenylethyl propionate, vinyl propionate, allyl propionate, methyl butyrate, ethyl butyrate, methyl valerate, ethyl valerate, methyl 3-methylbutanoate, ethyl 3-methylbutanoate, methyl caproate, ethyl caproate, methyl heptanoate, ethyl heptanoate, methyl caprylate, ethyl caprylate, methyl nonanoate, ethyl nonanoate, methyl caprate, ethyl caprate, methyl undecanoate, ethyl undecanoate, methyl phenylacetate, ethyl phenylacetate, methyl para-toluylacetate, ethyl para-toluylacetate, methyl naphthylacetate, ethyl naphthylacetate, methyl 3-phenylpropionate, ethyl 3-phenylpropionate, methyl vinyl acetate, ethyl vinyl acetate, methyl 4-pentenoate, ethyl 4-pentenoate, methyl 10-undecenoate, ethyl 10-undecenoate, methyl 3-butynoate, ethyl 3-butynoate, methyl 3-pentynoate, ethyl 3-pentynoate, methyl 3-hexynoate, and ethyl 3-hexynoate.

Among these, preferred carboxylate (4) are methyl acetate and methyl propionate, more preferred is methyl propionate.

Examples of the methylenating agent that may be employed in the present invention include, for example, formaldehyde, formaldehyde precursor and methylal. These may be used while containing a solvent.

Formaldehyde can be used in various forms. Formaldehyde can be supplied in the form of an aqueous solution such as formalin and 100% of formaldehyde, and formaldehyde precursor can be used in the case of supplying in the form of 100% of formaldehyde with difficulty. Formaldehyde precursor is not particularly limited if a compound such as to be easily decomposed into formaldehyde in a reaction system. Specific examples of formaldehyde precursor include trioxane and para-formaldehyde, preferably trioxane. These can also be used while diluted with an organic or inorganic solvent.

The amount of the methylenating agent is typically 0.01 to 10 moles, preferably 0.03 to 3 moles, more preferably 0.1 to 2 moles per mol of the carboxylic acid (1) or the carboxylate (4). In the case of using carboxylic anhydride (2), the amount of the methylenating agent that may be fed is usually approximately 0.02 to 20 moles, preferably 0.06 to 6 moles, more preferably 0.2 to 4 moles per mol of the carboxylic anhydride (2). As for formaldehyde precursor, the amount thereof is calculated in terms of formaldehyde.

α,β-unsaturated carboxylic acid of formula (3) is produced by reacting carboxylic acid (1) or carboxylic anhydride (2) with the methylenating agent.

In the case where $R^1$ denotes a hydrogen atom, namely, carboxylic acid (1) as a raw material or carboxylic anhydride (2) as a raw material are acetic acid or acetic anhydride respectively, the obtained α,β-unsaturated carboxylic acid (3), is acrylic acid, and in the case where $R^1$ denotes a methyl group, namely, carboxylic acid (1) as a raw material or carboxylic anhydride (2) as a raw material are propionic acid or propionic anhydride respectively, and α,β-unsaturated carboxylic acid (3) is methacrylic acid.

α,β-unsaturated carboxylate of formula (5) is produced by reacting carboxylate (4) with a methylenating agent. In the case where $R^1$ denotes a hydrogen atom, namely, carboxylate (4) as a raw material is acetate, and the obtained α,β-unsaturated carboxylate (5) is acrylate, and in the case where $R^1$ denotes a methyl group, namely, carboxylate (4) as a raw material is propionate, and α,β-unsaturated carboxylate (5) is methacrylate.

Examples of the metal of Group 13 of the Periodic Table of Elements include, for example, Al, Ga, In and Tl. Preferred is Al or Ga.

The metal is frequently used as oxide, which may be oxide of the metal of Group 13 of the Periodic Table of Elements alone, a mixture of two kinds or more of oxides of the metal of Group 13, or a mixture of oxide of the metal of Group 13 and other metal oxide, and may exist as complex oxide of the metals of Group 13 and other metal, preferably in a supported form on a carrier comprising other element(s).

Examples of the carrier include, for example, those that do not substantially contain the metal of Group 13, and specific examples thereof include, for example, $SiO_2$, $Al_2O_3$, $TiO_2$, $ZrO_2$, ZnO, $Fe_2O_3$, $CeO_2$, SiC, zeolite, and activated carbon. Preferred is $SiO_2$.

The catalyst in supported form can be produced, for example, by impregnating method, co-precipitating method, drying-up method and spray drying method. Among these, the impregnating method is preferred. Typically the impregnating method is carried out in such a way that a carrier is put into an aqueous solution of metal source compound of an element of Group 13 in the form of, for example, nitrate, and the resulting impregnated material is then collected, for example, by filtration to obtain a solid, which is then dried and calcined. The calcination temperature is generally in a range of 100 to 1300° C., preferably 200 to 1200° C. and more preferably 300 to 1000° C., approximately.

The content of the element of Group 13 of the Periodic Table of Elements is usually in a range of 0.001 to 5 weight % in terms of the metal of Group 13 with respect to the catalyst, and is more preferably 0.01 to 3 weight %, still more preferably 0.05 to 2 weight %, still further more preferably 0.05 to 1.5 weight % and much more preferably 0.1 to 1 weight %.

The reaction of the present invention can be performed in a continuous system or a batch system, preferred is a continuous system for industrial production.

The amount of carboxylic acid (1), carboxylic anhydride (2) or carboxylate (4) as raw materials for use in a continuous reaction system is generally approximately in a range of 0.1 to 100 g/hr per 1 g of a catalyst, preferably 0.3 to 20 g/hr.

In the reaction of the present invention, an inert gas can be supplied in addition to carboxylic acid (1), carboxylic anhydride (2) or carboxylate (4) and a methylenating agent. Examples of the inert gas include nitrogen, helium and argon, and nitrogen is typically used in view of costs.

The reaction is preferably performed at a temperature range of 150 to 500° C., more preferably 200 to 400° C. and further more preferably 250 to 350° C., approximately.

Reaction pressure is not particularly limited, and the reaction is typically performed approximately in a range of 0 MPa, which is equal to atmospheric pressure, to 10 MPa in gage pressure, more preferably 0.05 to 1 MPa.

Reaction mixture after completion of the reaction contains α,β-unsaturated carboxylic acid (3) or α,β-unsaturated carboxylate (5) as products, and may further contain unreacted raw materials and occasionally other impurities. α,β-Unsaturated carboxylic acid (3) or α,β-unsaturated carboxylate (5) may be purified from this reaction mixture, if necessary for further use, and a method therefore is not particularly limited and general methods such as distillation and extraction can be applied.

EXAMPLES

The present invention is further detailed hereinafter by way of examples and is not limited thereto.

Example 1

14.3 g of $SiO_2$ beads (CARiACT, manufactured by FUJI SILYSIA CHEMICAL LTD.) were projected into a solution of 1.02 g of $Ga(NO_3)_3.nH_2O$ (manufactured by WAKO PURE CHEMICAL INDUSTRIES, LTD.) in 200 g of ion-exchange water, and stirred at a temperature of 50° C. for 5 hours. The beads from which the solution was removed by decantation were dried at a temperature of 100° C. under reduced pressure and thereafter calcined for 5 hours in a muffle furnace adjusted to a temperature of 500° C. to prepare a catalyst. As a result of elemental analysis by IES-AES method, Ga content was 0.60 wt %.

5 g of the catalyst was introduced into a reaction tube made of SUS having an inside diameter of ¾ inch. A mixed liquid (in which 20 g of trioxane was dissolved in 230 g of propionic acid) of propionic acid (Special Grade, manufactured by KANTO KAGAKU) and trioxane (Special Grade, manufactured by KANTO KAGAKU) and nitrogen were introduced into the reaction tube heated to a temperature of 300° C. at a flow rate of 0.2 ml/min and 82 ml/min, respectively. The internal pressure of the reaction tube was maintained at 2 kg/cm² (equivalent to 0.2 MPa) in gage pressure by a back-pressure valve placed in the downstream part of the reaction tube.

When a reaction liquid collected in 1 to 3 hours after starting to supply the mixed liquid is subjected to quantitative analysis by gas chromatography (GC), the conversion of propionic acid was 8.6% and the selectivity of methacrylic acid in terms of the converted propionic acid was 92%.

Example 2

A catalyst was prepared in a similar manner as Example 1 except for projecting 14.3 g of $SiO_2$ beads into a solution, in which 1.92 g of $Ga(NO_3)_3.nH_2O$ (manufactured by WAKO PURE CHEMICAL INDUSTRIES, LTD.) was dissolved in 200 g of ion-exchange water. As a result of elemental analysis by IES-AES method, Ga content was 0.79 wt %.

When the reaction was performed in a similar manner as Example 1 except for using 5 g of the catalyst, the conversion of propionic acid was 7.8% and the selectivity of methacrylic acid in terms of the converted propionic acid was 91%.

Example 3

A catalyst was prepared in a similar manner as Example 1 except for projecting 14.3 g of $SiO_2$ beads into a solution, of 0.91 g of $Al(NO_3)_3.9H_2O$ (manufactured by WAKO PURE CHEMICAL INDUSTRIES, LTD.) in 200 g of ion-exchange water. As a result of elemental analysis by IES-AES method, Al content was 0.13 wt %.

When the reaction was performed in the same manner as Example 1 except for using 5 g of the catalyst, the conversion of propionic acid was 9.0% and the selectivity of methacrylic acid in terms of the converted propionic acid was 92%.

Example 4

A catalyst was prepared in a similar manner as Example 1 except for projecting 14.3 g of $SiO_2$ beads into a solution of 1.78 g of $Al(NO_3)_3.9H_2O$ (manufactured by WAKO PURE CHEMICAL INDUSTRIES, LTD.) in 200 g of ion-exchange water. As a result of elemental analysis by IES-AES method, Al content was 0.17 wt %.

When the reaction was performed in the same manner as Example 1 except for using 5 g of the catalyst, the conversion of propionic acid was 9.3% and the selectivity of methacrylic acid in terms of the converted propionic acid was 91%.

Example 5

A catalyst was prepared in a similar manner as Example 1 except for projecting 7.1 g of $SiO_2$ beads into a solution of 9.09 g of $Al(NO_3)_3 \cdot 9H_2O$ (manufactured by WAKO PURE CHEMICAL INDUSTRIES, LTD.) in 100 g of ion-exchange water. As a result of elemental analysis by IES-AES method, Al content was 0.61 wt %.

When the reaction was performed in the same manner as Example 1 except for using 5 g of the catalyst, the conversion of propionic acid was 8.8% and the selectivity of methacrylic acid in terms of the converted propionic acid was 87%.

Example 6

7.2 g of $SiO_2$ beads were projected into a solution of 1.18 g of $Al(NO_3)_3 \cdot 9H_2O$ (manufactured by WAKO PURE CHEMICAL INDUSTRIES, LTD.) in 100 g of ion-exchange water, and stirred at a temperature of 50° C. for 2 hours. The beads dried-up under reduced pressure were dried at a temperature of 100° C. under reduced pressure and thereafter calcined for 5 hours in a muffle furnace adjusted to a temperature of 500° C. to prepare a catalyst. As a result of elemental analysis by IES-AES method, Al content was 0.93 wt %.

When the reaction was performed in the same manner as Example 1 except for using 5 g of the catalyst, the conversion of propionic acid was 8.6% and the selectivity of methacrylic acid in terms of the converted propionic acid was 85%.

Example 7

14.3 g of $SiO_2$ beads (CARiACT, manufactured by FUJI SILYSIA CHEMICAL LTD.) were projected into a solution of 0.95 g of $Ga(NO_3)_3 \cdot nH_2O$ (manufactured by WAKO PURE CHEMICAL INDUSTRIES, LTD.) in 200 g of ion-exchange water, and stirred at a temperature of 50° C. for 5 hours. The beads from which the solution was removed by decantation were dried at a temperature of 100° C. under reduced pressure and thereafter calcined for 5 hours in a muffle furnace adjusted to a temperature of 500° C. to prepare a catalyst. As a result of elemental analysis by IES-AES method, Ga content was 1.11 wt %.

The reaction was carried out in a similar manner as in Example 1 except that 5 g of the catalyst was employed, the conversion of propionic acid was 9.0% and the selectivity of methacrylic acid in terms of the converted propionic acid was 90%.

Comparative Example 1

Ammonia water was added dropwise to a solution of 10.4 g of $Al(NO_3)_3 \cdot 9H_2O$ (manufactured by WAKO PURE CHEMICAL INDUSTRIES, LTD.) and 33.1 g of $Si(OEt)_4$ (manufactured by WAKO PURE CHEMICAL INDUSTRIES, LTD.) in a mixed liquid of 40 g of ion-exchange water and 320 g of ethanol so that the pH of the added solution became 8, and stirred at room temperature for 4 hours. White precipitate collected by pressure filtration was dried at a temperature of 100° C. under reduced pressure and thereafter calcined for 5 hours in a muffle furnace adjusted to a temperature of 500° C. to prepare a catalyst. As a result of the elemental analysis by IES-AES method, Al content was 6.42 wt %.

When the reaction was performed in the same manner as Example 1 except for using 5 g of the catalyst, the conversion of propionic acid was 9.2% and the selectivity of methacrylic acid in terms of the converted propionic acid was 76%.

What is claimed is:

1. A method of producing α,β-unsaturated carboxylic acid of formula (3)

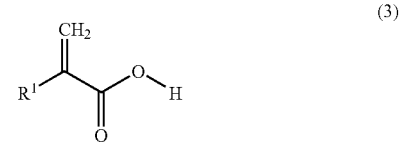

wherein $R^1$ denotes a hydrogen atom, an alkyl group, an aryl group, an aralkyl group, an alkenyl group or an alkynyl group, which method comprises reacting a carboxylic acid of formula (1)

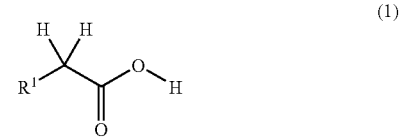

wherein $R^1$ denotes the same as the above, or carboxylic anhydride of formula (2)

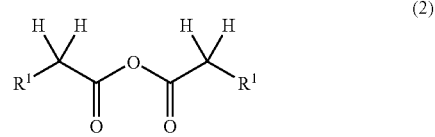

wherein $R^1$ denotes the same as the above, with a methylenating agent in a presence of a catalyst consisting essentially of, as a metal species, a metal selected from the group consisting of Al, Ga, In, and Tl, and the amount thereof is not more than 5 weight %.

2. A method of producing α,β-unsaturated carboxylate of formula (5)

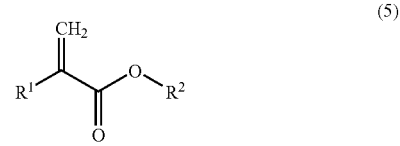

wherein $R^1$ denotes a hydrogen atom, an alkyl group, an aryl group, an aralkyl group, an alkenyl group or an alkynyl group, and $R^2$ denotes an alkyl group, an aryl group, an aralkyl group or an alkenyl group, which method comprise reacting a carboxylate of formula (4)

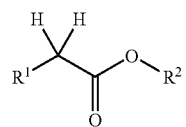

(4)

wherein $R^1$ and $R^2$ denote the same as the above, with a methylenating agent in a presence of a catalyst consisting essentially of, as a metal species, a metal selected from the group consisting of Al, Ga, In and Tl, and the amount thereof is not more than 5 weight %.

3. A method according to claim 1, wherein the metal is supported on silica.

4. A method according to claim 1, wherein the metal is aluminum or gallium.

5. A method according to claim 1, wherein the carboxylic acid of formula (1) according to claim 1 is acetic acid or propionic acid.

6. A method according to claim 1, wherein the methylenating agent is trioxane.

7. A method according to claim 1, wherein the amount of the metal contained in the catalyst is 0.05 to 1.5 wt %.

8. A method according to claim 2, wherein the catalyst is supported on silica.

* * * * *